United States Patent
Kakileti et al.

(10) Patent No.: US 12,141,984 B2
(45) Date of Patent: Nov. 12, 2024

(54) SYSTEM AND METHOD OF AUTOMATIC DETECTION OF HOTSPOT LOCATIONS IN BREAST THERMOGRAMS

(71) Applicant: Niramai Health Analytix Pvt. Ltd., Bangalore (IN)

(72) Inventors: Siva Teja Kakileti, Kakinada (IN); Geetha Manjunath, Bangalore (IN); Himanshu Jayant Kumar Madhu, Bangalore (IN)

(73) Assignee: NIRAMAI HEALTH ANALYTIX PVT. LTD, Bangalore (IN)

( * ) Notice: Subject to any disclaimer, the term of this patent is extended or adjusted under 35 U.S.C. 154(b) by 361 days.

(21) Appl. No.: 17/794,954

(22) PCT Filed: Jan. 23, 2021

(86) PCT No.: PCT/IN2021/050068
§ 371 (c)(1),
(2) Date: Jul. 23, 2022

(87) PCT Pub. No.: WO2021/149080
PCT Pub. Date: Jul. 29, 2021

(65) Prior Publication Data
US 2023/0058416 A1 Feb. 23, 2023

(30) Foreign Application Priority Data

Jan. 23, 2020 (CN) .............................. 202041002954

(51) Int. Cl.
*G06T 7/11* (2017.01)
*A61B 5/00* (2006.01)
(Continued)

(52) U.S. Cl.
CPC ............... *G06T 7/11* (2017.01); *A61B 5/015* (2013.01); *A61B 5/4312* (2013.01);
(Continued)

(58) Field of Classification Search
CPC ..... G06T 7/11; G06T 7/62; G06T 7/13; G06T 2207/10048; G06T 2207/20081;
(Continued)

(56) References Cited

U.S. PATENT DOCUMENTS 10,307,141 B2 * 6/2019 Venkataramani ......... G06T 7/68
2007/0213617 A1 * 9/2007 Berman ............... A61B 5/0091
600/473
(Continued)

*Primary Examiner* — William D Titcomb

(57) ABSTRACT

A system and method for automatically detecting a location of a plurality of hotspots from a thermal image of a breast region of a subject by (i) automatically detecting areolar points (x, y) from the thermal image of the breast region of the subject, (ii) automatically detecting a plurality of hotspot regions on the thermal image of the breast region of the subject by performing a hotspot region segmentation method, (iii) calculating a plurality of radial locations (ri, θi) of a plurality of hotspots on the hotspot region, (iv) automatically generating a text report based on the detected location of the plurality of hotspots and (v) providing the detected radial locations (ri, θi) of the plurality of hotspots as a text report to scan the plurality of hotspots only on the detected radial locations (ri, θi) instead of scanning in the entire breast region of the subject.

20 Claims, 9 Drawing Sheets

(51) Int. Cl.
*A61B 5/01* (2006.01)
*G06T 7/13* (2017.01)
*G06T 7/62* (2017.01)
*G16H 30/40* (2018.01)
*H04N 5/33* (2023.01)

(52) U.S. Cl.
CPC .............. *A61B 5/7267* (2013.01); *G06T 7/13* (2017.01); *G06T 7/62* (2017.01); *G16H 30/40* (2018.01); *H04N 5/33* (2013.01); *A61B 2562/04* (2013.01); *G06T 2207/10048* (2013.01); *G06T 2207/20081* (2013.01); *G06T 2207/30068* (2013.01)

(58) Field of Classification Search
CPC .......... G06T 2207/30068; G16H 30/40; A61B 5/105; A61B 5/4312; A61B 5/7267; A61B 2562/04; H04N 5/33
USPC ....................................................... 382/128
See application file for complete search history.

(56) References Cited

U.S. PATENT DOCUMENTS

| | | | |
|---|---|---|---|
| 2016/0035093 A1* | 2/2016 | Kateb | G02B 21/0012 382/131 |
| 2016/0278641 A1* | 9/2016 | Venkataramani | A61B 5/015 |
| 2016/0283658 A1* | 9/2016 | Venkataramani | G16H 50/30 |
| 2017/0249738 A1* | 8/2017 | Sivakumar | G16H 30/20 |
| 2018/0000462 A1* | 1/2018 | Venkataramani | G06T 7/11 |
| 2018/0005085 A1* | 1/2018 | Kakileti | G06V 10/764 |
| 2018/0020926 A1* | 1/2018 | Stang | A61B 5/015 600/439 |

* cited by examiner

SYSTEM AND METHOD OF AUTOMATIC DETECTION OF HOTSPOT LOCATIONS IN BREAST THERMOGRAMS

BACKGROUND

Technical Field

The present invention is directed towards hotspots detection in a thermal image conformant to standard operating procedure and, more particularly, to a system and method for automatically detecting a location of a plurality of hotspots from a thermal image of a breast region of a subject and generating a text report based on the detected location of the plurality of hotspots.

Description of the Related Art

Thermography is widely used for breast cancer screening in recent days. Thermography captures the amount of heat radiating from the surface of the body and measures the temperature patterns and distribution on the chest due to high metabolism associated with tumorous growth. There are several advantages of Breast thermography compared to other methods. It works on women of all age groups, does not involve radiation and is non-contact and hence painless. Thermography is a combination of thermal imaging of the body and its visual interpretation. However, thermography did not become very prominent as it needs high expertise to interpret thermal images manually. Also, manual interpretation is very difficult due to the presence of thousands of color pixels. Hence, computer-aided analysis of thermal images is becoming necessary especially to convert these thermal images into quantifiable parameters to empower doctors in the final diagnosis.

The computer-aided thermal analysis uses localization techniques to identify the exact location of a lesion, as most lesions exhibit high-temperature spots at the location. This localization helps ultrasound to focus only on the detected lesions and thus reducing the ultrasound screening time. Without the localization technique, the sonographer has to hover over the entire breast and will find it very difficult to find small lesions. In some scenarios, more than one hotspot may be identified for a single lesion and it is not possible to detect which hotspot to focus on without a detailed analysis of the hotspot. This localisation may provide information to enable correlation with other imaging modalities like MRI, mammography etc.

Hence, there is a need for an automated system and method to automatically detect a location of a plurality of hotspots from a thermal image of a breast region of a subject and generating a text report based on the detected location of the plurality of hotspots.

SUMMARY

In view of the foregoing, embodiment herein provides a system for automatically detecting a location of a plurality of hotspots from a thermal image of a breast region of a subject. The system includes a storage device and a processor. The processor retrieves machine-readable instructions from the storage device which, when executed by the processor, enable the processor to (i) receive the thermal image of the breast region of the subject, which represents a temperature distribution on the breast region of the subject as pixels in the thermal image, (ii) automatically detect areolar points from the thermal image of the breast region of the subject, (iii) automatically detect a plurality of hotspot regions on the thermal image of the breast region of the subject by performing a hotspot region segmentation method, (iv) calculate a plurality of radial locations (ri, θi) of a plurality of hotspots on the hotspot region by estimating a radial distance (ri) and a radial angle (θi) using the areolar points as a reference origin point and (v) automatically generate a text report based on the detected location of the plurality of hotspots. The thermal image is captured using at least one of a thermal imaging camera or a wearable device. The thermal imaging camera or a wearable device includes (i) an array of sensors that convert infrared energy into electrical signals on a per-pixel basis, (ii) a lens that focuses the infrared energy from the subject's breast region onto the array of sensors and (iii) a specialized processor that processes the detected temperature values into at least one block of pixels to generate the thermal image. The array of sensors detect temperature values from the subject's breast region. The hotspot region segmentation method segments the plurality of hotspot regions from the thermal image.

In some embodiments, the processor is configured to train the first machine learning model by providing a plurality of thermal images and the corresponding areolar points of different patients as training data to obtain the trained first machine learning model.

In some embodiments, the processor is configured to rank the plurality of hotspots on the thermal image by identifying a hotspot area, a maximum temperature, a hotspot shape, and a hotspot boundary and ranking the plurality of hotspots based on their severity or importance for generating the text report.

In some embodiments, the processor is configured to employ a second machine learning model that ranks the plurality of hotspots based on their severity or importance. The second machine learning model is trained to identify the severe/important hotspots by providing severe/important hotspots and the corresponding ranking of different patients as training data to obtain a trained second machine learning model.

In some embodiments, the automatically generated text report includes one or more modes of depicting positions of the plurality of hotspots including at least one of quadrants, clock positions, the radial distance (ri), radial zone or a schematic pictorial representations calculated based on the areolar points.

In some embodiments, the processor is configured to identify a quadrant of each hotspot by dividing the thermal image of the breast region of the subject into four equal circular sectors using the areolar points as a centre of a reference coordinate system and using the reference coordinate system to detect the quadrant of the hotspot.

In some embodiments, the processor is configured to identify the clock position of each hotspot by detecting an angle formed by the areolar points and a centroid of the hotspot with the horizontal axis and converting the angle into the clock position of that hotspot.

In some embodiments, the processor is configured to detect the plurality of hotspot regions on the thermal image of the breast region of the subject by (i) determining a first pixel region m within a selected region of interest with a temperature $T^1_{pixel}$, where $T_2 \le T^1_{pixel} \le T_1$, (ii) determining a second pixel region $m_2$ within the selected region of interest with a temperature $T^2_{pixel}$, where $T_3 \le T^2_{pixel}$ and (iii) detecting the plurality of hotspot regions using the first pixel region $m_1$ and the second pixel region $m_2$ with AND or OR rules, wherein $T_1$, $T_2$ and $T_3$ are temperature threshold obtained from the temperature distribution.

In some embodiments, the processor is configured to detect the plurality of hotspot regions on the thermal image of the breast region of the subject using a third machine learning model. The third machine learning model is trained by providing a plurality of thermal images and the corresponding hotspot regions associated with different patients as training data to obtain a trained third machine learning model.

In some embodiments, the processor is configured to generate the text report using a text conversion unit based on the radial distance, quadrant estimation, radial zone estimation and the clock position estimation. The text report is updated to a database of the system along with annotated thermal images of the subject and/or schematic of the breast for providing the locations of the plurality of hotspots as a text report.

In some embodiments, the system is communicatively connected to a device (e.g. a scanner) and provides the detected radial locations (ri, θi) of the plurality of hotspots as a text report to scan the plurality of hotspots only on the detected radial locations (ri, θi) instead of scanning the entire breast region of the subject.

In some embodiments, the areolar points are detected by at least one of (i) identifying a potential areolar region on the thermal image by detecting a boundary that is close to a circular or an ellipse shape in the breast region using an areolar detection module, (ii) identifying the areolar points in the thermal image by providing the thermal image that is captured as an input to the first machine learning model using a first machine learning model or (iii) manually identifying the circular or the ellipse shape in the breast region.

In another aspect, method for automatically detecting a location of a plurality of hotspots from a thermal image of a breast region of a subject includes (i) receiving the thermal image of a body of a subject, which represents a temperature distribution on the body of the subject as pixels in the thermal image, (ii) automatically detecting areolar points from the thermal image of the breast region of the subject, (iii) automatically detecting a plurality of hotspot regions on the thermal image of the breast region of the subject by performing a hotspot region segmentation method. (iv) calculating a plurality of radial locations (ri, θi) of a plurality of hotspots on the hotspot region by estimating a radial distance (ri) and a radial angle (θi) using the areolar points as a reference origin point and (v) automatically generating a text report based on the detected location of the plurality of hotspots. The hotspot region segmentation method segments the plurality of hotspot regions from the thermal image.

In some embodiments, the areolar points are detected by at least one of (i) identifying, using an areolar detection module, a potential areolar region on the thermal image by detecting a boundary that is close to a circular or an ellipse shape in the breast region, (ii) identifying, using a first machine learning model, the areolar points in the thermal image by providing the thermal image that is captured as an input to the first machine learning model or (iii) manually identifying the circular or the ellipse shape in the breast region.

In some embodiments, the first machine learning model is trained by providing a plurality of thermal images and the corresponding areolar points of different patients as training data to obtain the trained first machine learning model.

In some embodiments, the method includes the step of ranking the plurality of hotspots on the thermal image by identifying a hotspot area, a maximum temperature, a hotspot shape, and a hotspot boundary and ranking the plurality of hotspots based on their severity or importance for generating the text report.

In some embodiments, the method includes the step of employing a second machine learning model that ranks the plurality of hotspots based on their severity or importance. The second machine learning model is trained to identify the severe/important hotspots by providing severe/important hotspots and the corresponding ranking of different patients as training data to obtain a trained second machine learning model.

In some embodiments, the automatically generated text report includes one or more modes of depicting positions of the plurality of hotspots including at least one of quadrants, clock positions, the radial distance (ri), radial zone or a schematic pictorial representations calculated based on the areolar points.

In some embodiments, the method includes identifying a quadrant of each hotspot by dividing the thermal image of the breast region of the subject into four equal circular sectors using the areolar points as a centre of a reference coordinate system and using the reference coordinate system to detect the quadrant of the hotspot.

In some embodiments, the method includes the steps of identifying a clock position of each hotspot by detecting an angle formed by the areolar points and a centroid of the hotspot with the horizontal axis and converting the angle into the clock position of that hotspot.

In some embodiments, the hotspot regions on the thermal image of the breast region of the subject are detected by (i) determining a first pixel region $m_1$ within a selected region of interest with a temperature $T^1_{pixel}$, where $T_2 \le T^1_{pixel} \le T_1$, (ii) determining a second pixel region $m_2$ within the selected region of interest with a temperature $T^2_{pixel}$, where $T_3 \le T^2_{pixel}$ and (iii) detecting the plurality of hotspot regions using the first pixel region $m_1$ and the second pixel region $m_2$ with AND or OR rules, wherein $T_1$, $T_2$ and $T_3$ are temperature threshold obtained from the temperature distribution.

In some embodiments, the plurality of hotspot regions on the thermal image of the breast region of the subject are detected using a third machine learning model. The third machine learning model is trained by providing a plurality of thermal images and the corresponding hotspot regions associated with different patients as training data to obtain a trained third machine learning model.

In some embodiments, the method includes providing the detected radial locations (ri, θi) of the plurality of hotspots as a text report to scan the plurality of hotspots only on the detected radial locations, (ri, θi) instead of scanning the entire breast region of the subject.

The system ensures the correct segmentation of the breast region with better accuracy. The system enables automatic selection of required views from the videos and guides a technician to capture the perfect view of the thermal image. The system may automate the thermal image capturing by obtaining feedback from the tagging classifier/the view angle estimator. A set of frames from a video may be passed as a batch input to the system and the system may predict a view angle to enable segmentation of the breast region in all frames. The system performs an automated image capturing with minimal or no human intervention during image capture. This can also help in reducing the scan time of the ultrasound machine and improve the search of the hotspot locations.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

Figure 1:
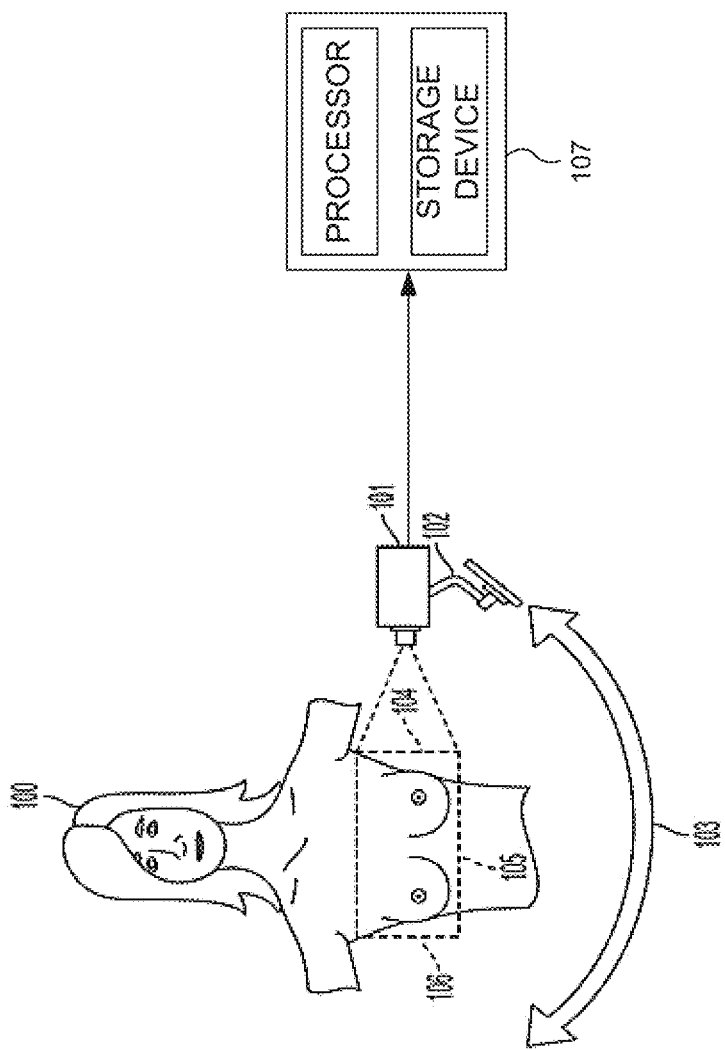
FIG. 1 illustrates an example female patient with a thermal imaging camera mourned on a slidable and axially rotatable robotic arm for moving the thermal camera along a semi-circular trajectory from side-to-side in front of the patient according to some embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system and a method for automatically detecting a location of a plurality of hotspots from a thermal image of a breast region of a subject and generating a text report based on the detected location of the plurality of hotspots. Referring now to the drawings, and more particularly to FIGS. 1 through 8, where similar reference characters denote corresponding features consistently throughout the figures, there are shown preferred embodiments.

A "person" and "subject" refers to either a male or a female. Gender pronouns are not to be viewed as limiting the scope of the appended claims strictly to females. Moreover, although the term "person" or "patient" or "subject" is used interchangeably throughout this disclosure, it should be appreciated that the person undergoing breast cancer screening may be something other than a human such as, for example, a primate. Therefore, the use of such terms is not to be viewed as limiting the scope of the appended claims to humans.

A "breast area" refers to the tissue of the breast and may further include surrounding tissue as is deemed appropriate for breast cancer screening. Thermal images are the capture of the breast area in various view angles which include a mediolateral view (center chest), a mediolateral oblique (angular) view, and a lateral (side) view, as are generally understood in the medical imaging arts. It should be appreciated that the mediolateral view is a supplementary mammographic view which generally shows less breast tissue and pectoral muscle than the mediolateral oblique view. FIG. 1 shows the breast area of a female 100. It should be appreciated that the patient may be stationary while the camera moves about the patient, or the patient can move while the camera remains stationary, or the patient and the camera may move to capture the appropriate view angles as desired.

A "thermal camera" refers to either a still camera or a video camera with a lens that focuses infrared energy from objects in a scene onto an array of specialized sensors which convert infrared energy across a desired thermal wavelength band into electrical signals on a per-pixel basis and which output an array of pixels with colours that correspond to temperatures of the objects in the image.

A "thermographic image" or simply a "thermal image" is an image captured by a thermal camera. The thermographic image comprises an array of color pixels with each color being associated with temperature. Pixels with a higher temperature value are displayed in the thermal image in a first color and pixels with a lower temperature value are displayed in a second color. Pixels with temperature values between the lower and higher temperature values are displayed in gradations of color between the first and second colors.

"Receiving a thermal image" of a patient for cancer screening is intended to be widely construed and includes retrieving, capturing, acquiring, or otherwise obtaining video image frames.

"Analyzing the thermographic image" means to identify a plurality of points (PN) in the image.

A "software interface tool" is a composite of functionality for tumor detection and/or tumor classification using a plurality of user-selectable objects displayed on a display device such as a touchscreen display. Various embodiments of the software interface tool perform manual, semi-automatic, and automatic selection of a block of pixels in the thermal image for screening.

FIG. 1 illustrates an example female patient with a thermal imaging camera mounted on a slidable and axially rotatable robotic arm for moving the thermal camera along a semi-circular trajectory from side-to-side in front of the patient according to some embodiments herein. The thermal imaging camera 101 is mounted on a slidable and axially rotatable robotic arm 102 capable of moving the thermal imaging camera 101 along a semi-circular trajectory 103 in the front of the patient/subject from side-to-side such that thermographic images may be captured in a right-side view 104, a front view 105, and a left-side view 106, and various oblique angles in between. The thermal imaging camera 101 can be a single-band infrared camera, a multi-band infrared camera in the thermal range, and a hyperspectral infrared camera in the thermal range. The resolution of the thermal imaging camera 101 is effectively the size of the pixel. Smaller pixels mean that the resulting image has a higher resolution and thus better spatial definition. Although, the thermal imaging camera 101 offers a relatively large dynamic range of temperature settings, it is preferable that the camera's temperature range be relatively small, centered around the person's body surface temperature so that small temperature variations are amplified in terms of pixel color changes in order to provide a better measure of temperature variation. Thermal imaging cameras are readily available in various streams of commerce. The thermal imaging camera 101 is communicatively connected to a system 107 which process the thermal image captured by the thermal imaging camera 101 for automatically detecting a location of a plurality of hotspots from a thermal image of a breast region of a subject and optionally for controlling a device/a scanner by providing the locations of the plurality of hotspots as a text report to scan the plurality of hotspots only instead of scanning the entire breast region of the subject.

Figure 2:
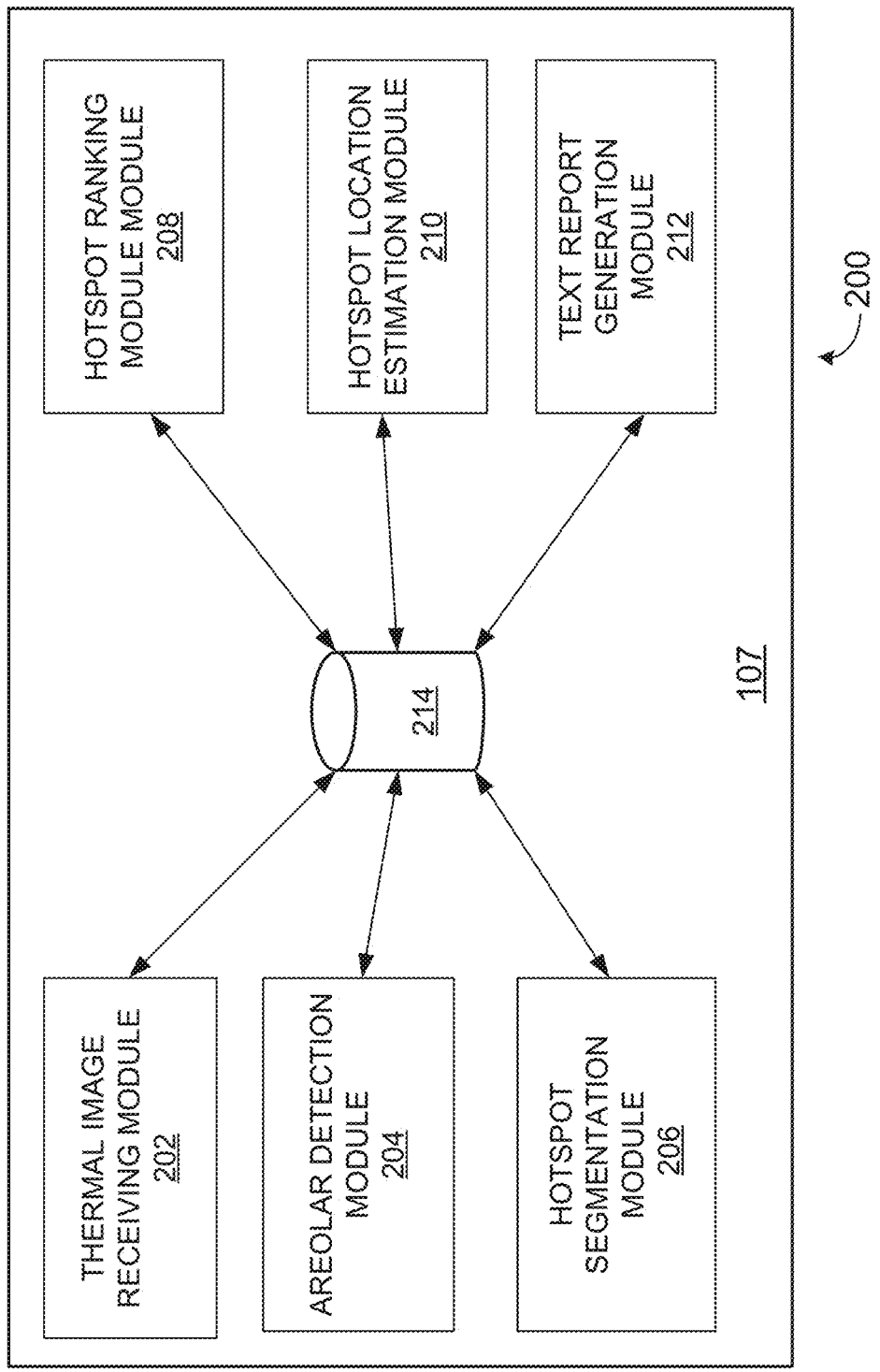
FIG. 2 illustrates an exploded view of a system for automatically detecting a location of a plurality of hotspots from a thermal image of a breast region of a subject according to some embodiments herein.

FIG. 2 illustrates an exploded view 200 of the system 107 for automatically detecting a location of a plurality of hotspots from a thermal image of a breast region of a subject according to some embodiments herein. The block diagram 200 of the system 107 includes a thermal image receiving module 202, an areolar detection module 204, a hotspot segmentation module 206, a hotspot ranking module 208, a hotspot location estimation module 210, a text report generation module 212 and a database 214. The thermal image receiving module 202 receives a thermal image of a body of a subject/patient. In some embodiments, the thermal image represents a temperature distribution on the body of the subject as pixels in the thermal image with the highest temperature value being displayed in a first color and pixels with the lowest temperature value being displayed in a second color. The pixels with temperature values between the lowest and highest temperature values being displayed in gradations of color between the first and second colors. In some embodiments, the thermal image is captured using at least one of a thermal imaging camera 101 or a wearable device that is connected with the system 107. In some embodiments, the thermal imaging camera 101 or a wearable device includes an array of sensors, a lens and a specialized processor. The array of sensors converts infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the thermal image. The areolar detection module 204 automatically detects areolar points from the thermal image of the breast region of the subject. In some embodiment, the areolar points are used to determine a reference point on the thermal image. The areolar detection module 204 detects the areolar points by identifying a potential areolar region on the thermal image by detecting a boundary that closes to a circular or an ellipse shape in the breast region. In some embodiments, the areolar points are detected using a first machine learning model by identifying the areolar points in the thermal image by providing the thermal image that is captured as an input to the first machine learning model. The first machine learning model is trained by providing a plurality of thermal images and the corresponding areolar points of different patients as training data to obtain a trained first machine learning model.

The hotspot segmentation module 206 detects a plurality of hotspot regions on the thermal image of the breast region of the subject by performing a hotspot region segmentation method. In some embodiments, the hotspot region segmentation method segments the plurality of hotspot regions from the thermal image. The hotspot segmentation module 206 performs the hotspot region segmentation method to detect the plurality of hotspot regions on the thermal image of the breast region of the subject. The hotspot region segmentation method includes steps of (i) determining a first pixel region $m_1$ within a selected region of interest with a temperature $T^1_{pixel}$, where $T_2 \leq T^1_{pixel} \leq T_1$, (ii) determining a second pixel region $m_2$ within the selected region of interest with a temperature $T^2_{pixel}$, where $T_3 \leq T^2_{pixel}$ and (iii) detecting the plurality of hotspot regions using the first pixel region $m_1$ and the second pixel region $m_2$ with AND or OR rules, wherein $T_1$, $T_2$ and $T_3$ are temperature threshold obtained from the temperature distribution. In some embodiments, the plurality of hotspot regions are detected using a second machine learning model. The second machine learning model is trained by providing severe/important hotspots and the corresponding ranking of different patients as training data to obtain a trained second machine learning model. In an embodiment, the second machine learning model is trained to identify the severe/important hotspots. The second machine learning model identifies the plurality of hotspot regions from the thermal image by providing the thermal image that is captured as an input to the second machine learning model.

The hotspot location estimation module 210 calculates a plurality of radial locations (ri, θi) of a plurality of hotspots on the hotspot region by estimating a radial distance (ri) and a radial angle (θi) using the areolar points as a reference origin point.

In some embodiments, the hotspot location estimation module 210 identifies a quadrant of each hotspot by dividing the thermal image of the breast region of the subject into four equal circular sectors using the areolar points as a centre of a reference coordinate system and using the reference coordinate system to detect the quadrant of the hotspot. In some embodiments, the reference coordinate system is used to detect the hotspot area present in each quadrant. The hotspot location estimation module 210 identifies the clock position of each hotspot by detecting an angle formed by the areolar points and a centroid of the hotspot with the horizontal axis and converting the angle into the clock position of that hotspot. In some embodiments, the detected locations of the plurality of hotspot locations are annotated in the thermal image of the breast region of the subject.

The hotspot ranking module 208 ranks the plurality of hotspots detected on the thermal image of the subject by identifying a hotspot area, a maximum temperature, a hotspot shape, and a hotspot boundary and ranking the plurality of hotspots based on their severity or importance for generating the text report. In some embodiments, the system 107 employs a second machine learning model that ranks the plurality of hotspots based on their severity or importance. In some embodiments, the second machine learning model is trained to identify the severe/important hotspots by providing severe/important hotspots and the corresponding ranking of different patients as training data to obtain a trained second machine learning model.

The text report generation module 212 generates a text report based on the detected location of the plurality of hotspot locations. In some embodiments, the system 107 converts the annotated thermal images into a text using an image to text conversion techniques. The system 107 is communicatively connected with a device/a scanner and provides the text report to the device/scanner to scan the plurality of hotspots only on the detected hotspot location instead of scanning the entire breast region of the subject in higher accuracy. In some embodiments, the device/scanner is adapted to scan the plurality of hotspots based on the text report that is received as an input from the system 107. In some embodiments, the automatically generated text report includes one or more quadrants, clock positions, and radial distance (ri) of the plurality of hotspots calculated based on the areolar points to detect the location of the plurality of hotspots.

Figure 3:
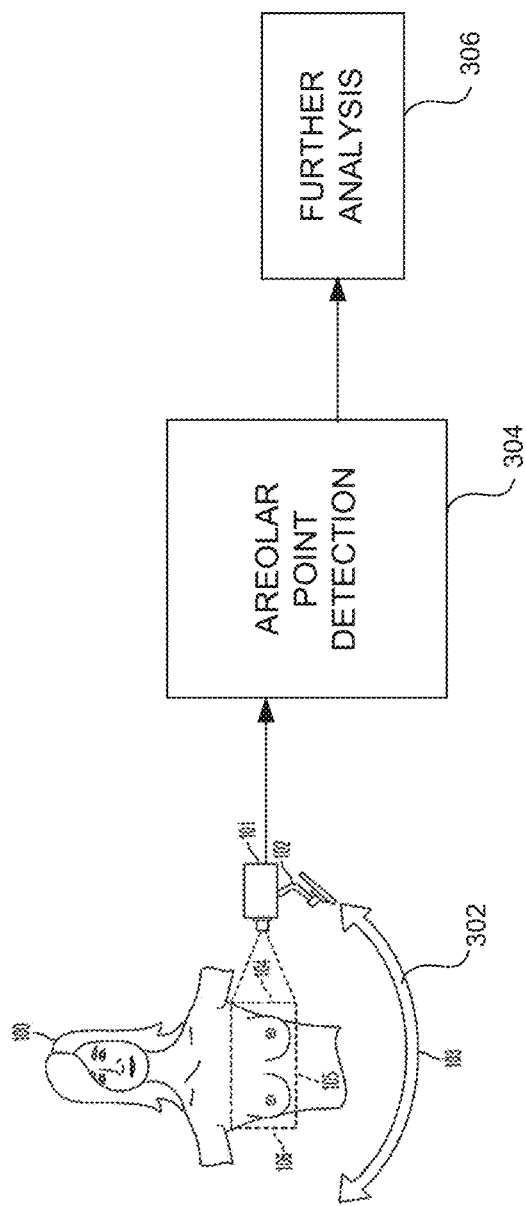
FIG. 3 illustrates an exemplary process flow of areolar points detection from a thermal image of a subject to determine a reference point on the thermal image according to some embodiments herein.

FIG. 3 illustrates an exemplary process flow of the detection of the areolar points from a thermal image of a subject to determine a reference point on the thermal image according to some embodiments herein. At step 302, the thermal image is captured using a thermal imaging camera. In some embodiment, the thermal image may be received or retrieved from a remote device over a network, or from a media such as a CDROM or DVD. The thermal image may be downloaded from a web-based system or an application that makes a video available for processing in accordance with the methods disclosed in herein. The thermal image may also be received from an application such as those which are available for handheld cellular devices and processed on the cell phone or other handheld computing devices such as an iPad or Tablet-PC. The thermal image may be received directly from a memory or storage device of the imaging device that is used to capture that thermal image or a thermal video.

At step 304, the areolar points are detected to determine the centroid of the thermal image by identifying a potential areolar region on the thermal image by detecting a boundary that closes to a circular or an ellipse shape in the breast region. In some embodiments. The areolar points are detected using at least one of the areolar detection module 204 or the first machine learning model. The areolar detection module 204 detects a boundary that closes to a circular or an ellipse shape to identify a potential areolar region on the thermal image of the subject. In some embodiments, the areolar points is used as a reference point on a breast region of the thermal image of the subject to detect the location of the plurality of hotspots. The first machine learning model detects the areolar points by providing a plurality of thermal images and the corresponding areolar points of different patients as training data to obtain a trained first machine learning model. At step 306, the detected areolar points are provided to system 107 for further analysis.

Figure 4:
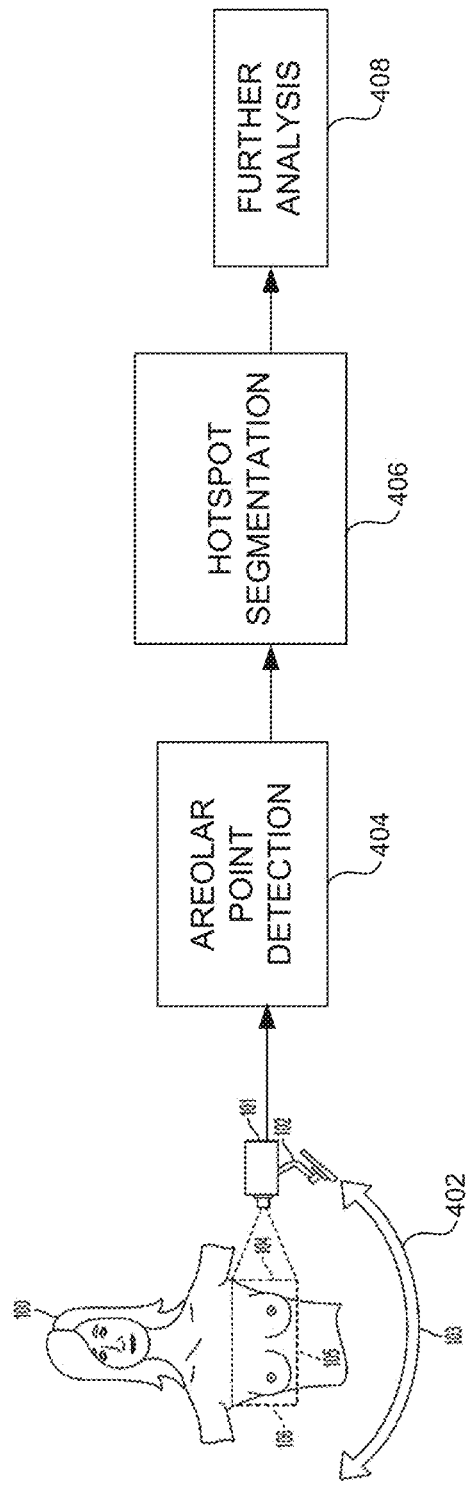
FIG. 4 illustrates an exemplary process flow of a hotspot segmentation to detect a plurality of hotspot region on the thermal image of the subject according to some embodiments herein.

FIG. 4 illustrates an exemplary process flow of a hotspot segmentation to detect a plurality of the hotspot region on the thermal image of the subject according to some embodiments herein. At step 402, the thermal image is captured using a thermal imaging camera. At step 404, the areolar points are detected to determine the centroid of the thermal image. The areolar points are referred to as a reference point to detect a location of the plurality of the hotspots in the hot spot region of the thermal image. At step 406, the hotspot segmentation is performed by: (i) determining a first pixel region $m_1$ within a selected region of interest with a temperature $T^1_{pixel}$, where $T_2 \leq T^1_{pixel} \leq T_1$, (ii) determining a second pixel region $m_2$ within the selected region of interest with a temperature $T^2_{pixel}$, where $T_3 \leq T^2_{pixel}$ and (iii) detecting the plurality of hotspot regions using the first pixel region $m_1$ and the second pixel region $m_2$ with AND or OR rules, wherein $T_1$, $T_2$ and $T_3$ are temperature threshold obtained from the temperature distribution. At step 408, the hotspot segmented thermal images are provided to the system 107 for further analysis.

Figure 5:
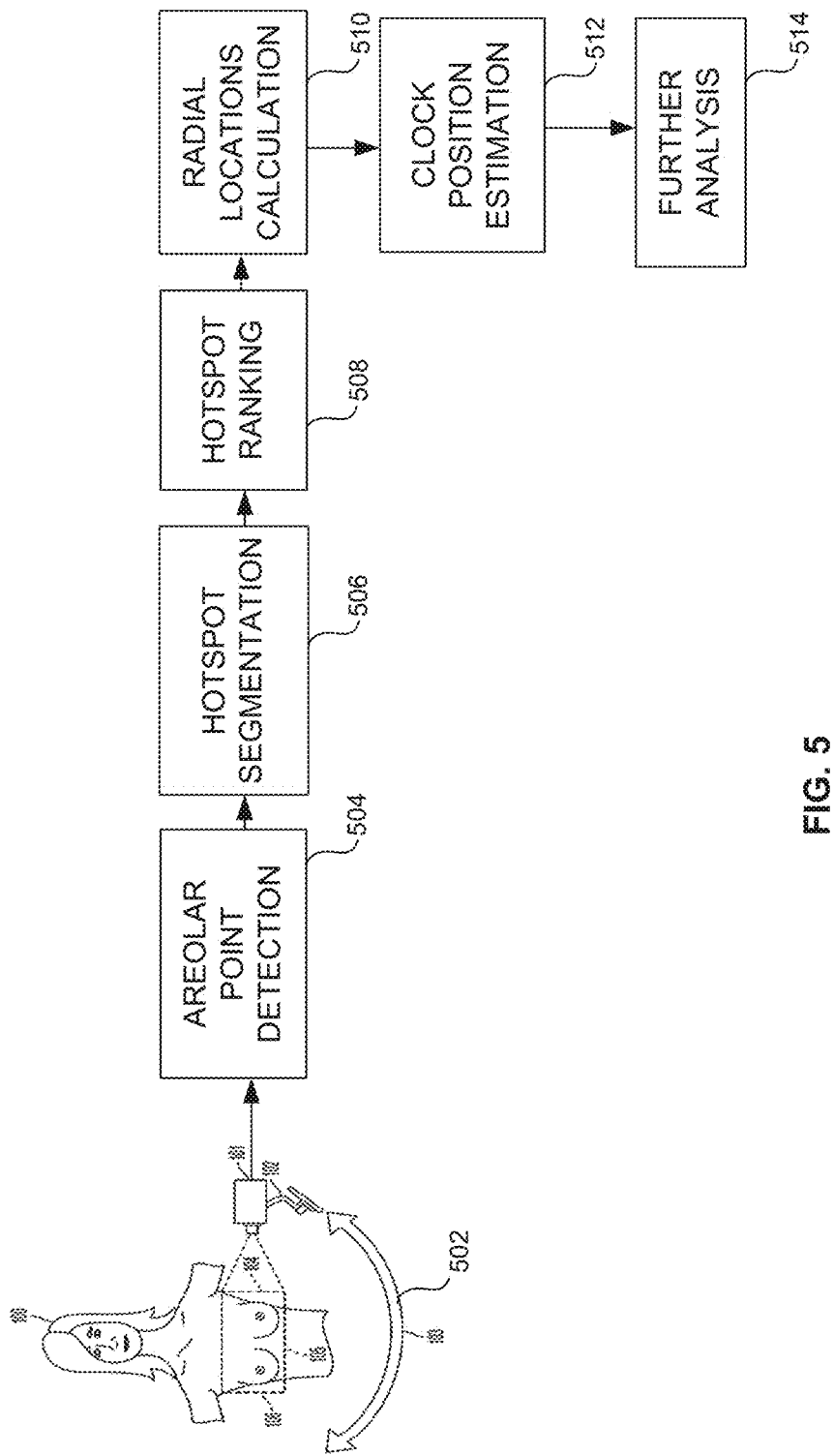
FIG. 5 illustrates an exemplary process flow of detection of a location of a plurality of hotspots on the hotspot region using the areolar points according to some embodiments herein.

FIG. 5 illustrates an exemplary process flow of detection of a location of a plurality of hotspots on the hotspot region using the areolar points according to some embodiments herein. At step 502, the thermal image is captured using a thermal imaging camera. At step 504, the areolar points are detected to determine the centroid of the thermal image. At step 506, the plurality of hotspot regions on the thermal image of the breast region of the subject is detected by performing a hotspot region segmentation method. At step 508, the plurality of hotspots detected on the thermal image of the subject is ranked by identifying a hotspot area, a maximum temperature, a hotspot shape, and a hotspot boundary and ranking the plurality of hotspots based on their severity or importance for generating the text report. In an embodiment, the system 107 employs a second machine learning model to rank the plurality of hotspots based on their severity or importance. In some embodiments, the second machine learning model is trained to identify the severe/important hotspots by providing severe/important hotspots and the corresponding ranking of different patients as training data to obtain a trained second machine learning model.

At step 510, a plurality of radial locations (ri, θi) of a plurality of hotspots on the hotspot region is calculated by estimating a radial distance (ri) and a radial angle (θi) using the areolar points as a reference origin point. In an embodiment, a quadrant of each hotspot is identified by dividing the thermal image of the breast region of the subject into four equal circular sectors using the areolar points as a center of a reference coordinate system and using the reference coordinate system to detect the quadrant of the hotspot. At step 512, the clock position of each hotspot is identified by detecting an angle formed by the areolar points and a centroid of the hotspot with the horizontal axis and converting the angle into the clock position of that hotspot. At step 514, detected locations of the plurality of hotspot locations are provided to the system 107 for further analysis.

Figure 6A:
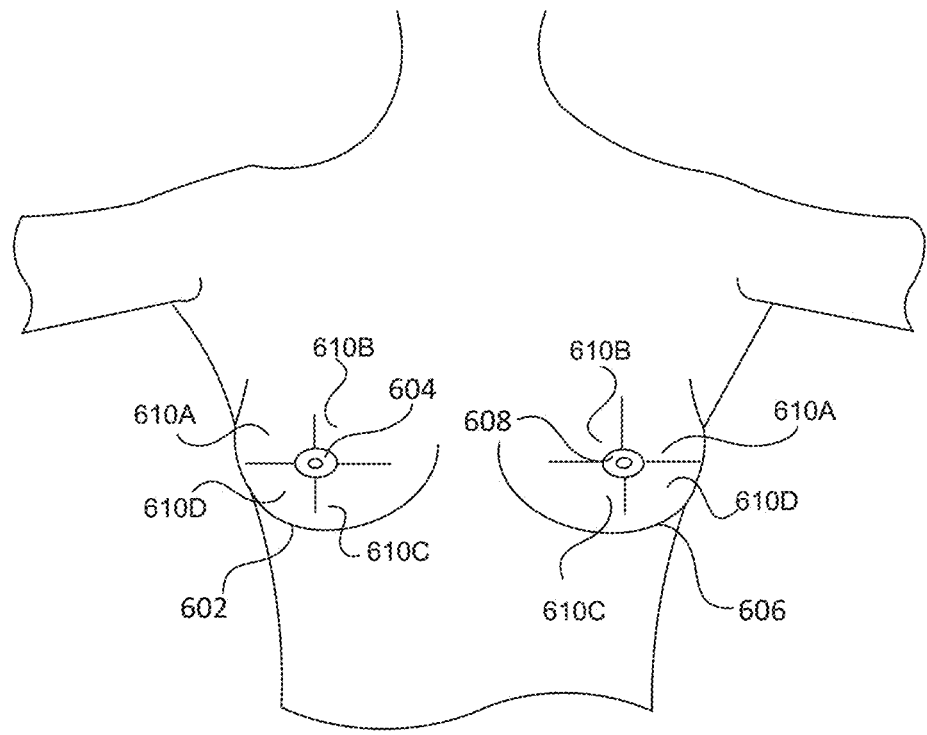
FIGS. 6A and 6B are an exemplary quadrant and clock position on a thermal image of a breast region of a subject according to some embodiments herein.
Figure 6B:
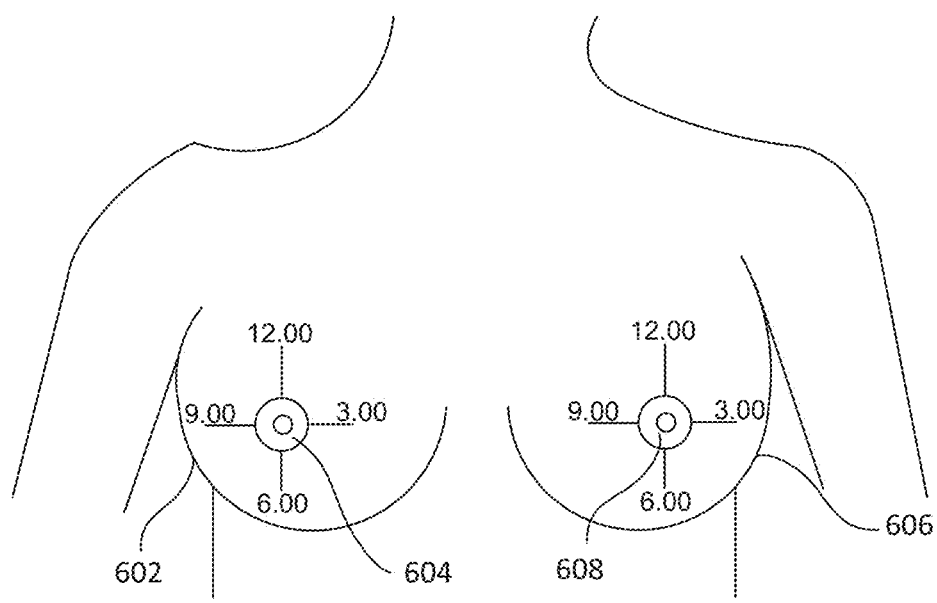
Figure 6C:
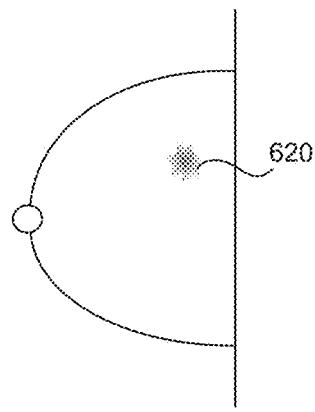
FIG. 6C is an exemplary mammography view of a thermal image of a breast region of a subject with a hotspot location according to some embodiments herein.

FIGS. 6A and 6B is an exemplary quadrant and clock position on a thermal image of a breast region of a subject according to some embodiments herein. The thermal image of the breast region of the subject includes a right breast 602, a right areolar point 604 which is represented as x, a left breast 606 and a left areolar point 608 which is represented as y. The areolar points (x, y) (i.e. 604 and 608) is detected by the areolar detection module 204 or the first machine learning model. Each breast region includes quadrants that include at least one of (i) an upper outer quadrant (UOQ) 610A, (ii) an upper inner quadrant (UIQ) 610B, (iii) a lower inner quadrant (LIQ) 610C or (iv) a lower outer quadrant (LOQ) 610D. In some embodiments, the clock position may locate in at least one quadrant of the breast region, FIG. 6C is an exemplary mammography view of the thermal image of the breast region of the subject with a hotspot location according to some embodiments herein. The hotspot location on a hot spot region is detected using a radial locations (ri, θi). In some embodiments, the radial locations (ri, θi) of the hotspot on the hotspot region is determined using the areolar points 604 and 608 as a reference origin point.

Figure 6D:
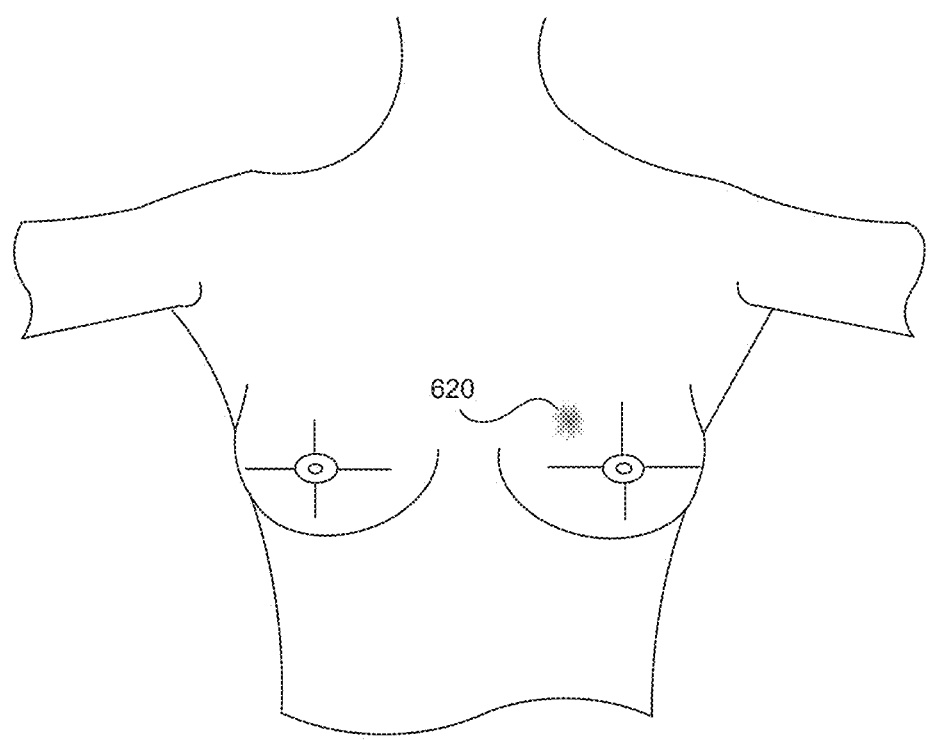
FIG. 6D is an exemplary silhouette view of a thermal image of a breast region of a subject with a hotspot location according to some embodiments herein.

FIG. 6D is an exemplary front view of the thermal image of the breast region of the subject with the hotspot location on a breast silhouette according to some embodiments herein. The hotspot location on the hot spot region is determined using the radial locations (ri, θi). In some embodiments, the radial locations (ri, θi) of the hotspot on the hotspot region is determined on the breast silhouette using the areolar points 604 and 608 as a reference origin point.

Figure 7:
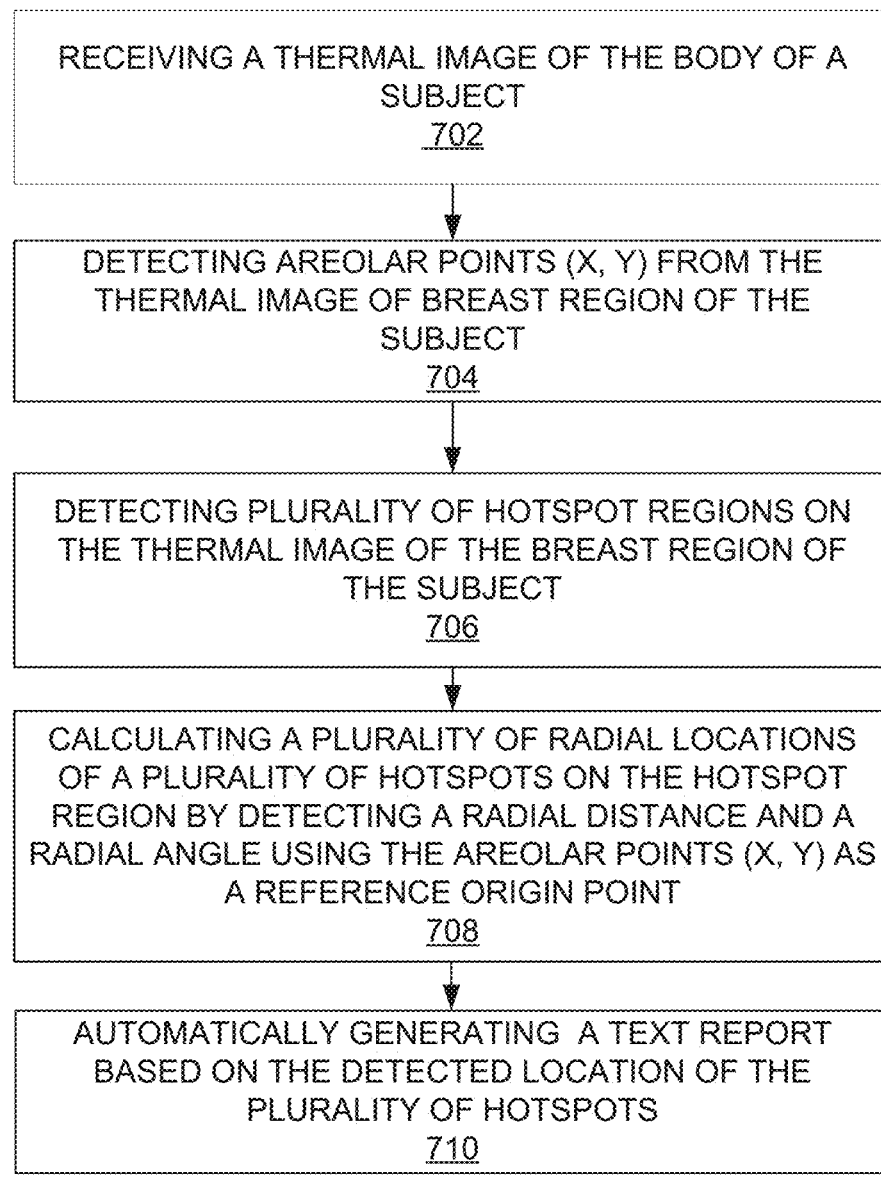
FIG. 7 illustrates a flow diagram of one embodiment of the present method for automatically detecting a location of a plurality of hotspots from a thermal image of a breast region of a subject according to some embodiments herein.

With reference to FIGS. 6A and 6B. FIG. 7 illustrates a flow diagram of one embodiment of the present method for automatically detecting a location of a plurality of hotspots from a thermal image of a breast region of a subject according to some embodiments herein. At step 702, the thermal image of the body of the subject is received. In some embodiments, the thermal image represents a temperature distribution on the body of the subject as pixels in the thermal image, At step 704, the areolar points (x, y) are detected from the thermal image of the breast region of the subject. In some embodiments, the areolar points (x, y) are detected by (i) identifying, using the areolar detection module 204, a potential areolar region on the thermal image by detecting a boundary that is close to a circular or an ellipse shape in the breast region, or (ii) identifying, using the first machine learning model, the areolar points (x, y) in the thermal image by providing the thermal image that is captured as an input to the first machine learning model. At step 706, a plurality of hotspot regions on the thermal image of the breast region of the subject is detected by performing the hotspot region segmentation method. At step 708, a plurality of radial locations (ri, θi) of a plurality of hotspots on the hotspot region is calculated by estimating a radial distance (ri) and a radial angle (θi) using the areolar points (x, y) as a reference origin point. At step 710, automatically generating the text report based on the detected location of the plurality of hotspots. In some embodiments, the detected radial locations (ri, θi) of the plurality of hotspots are provided as a text report to a device/a scanner for scanning the plurality of hotspots only on the detected radial locations (ri, θi) instead of scanning the entire breast region of the subject.

Figure 8:
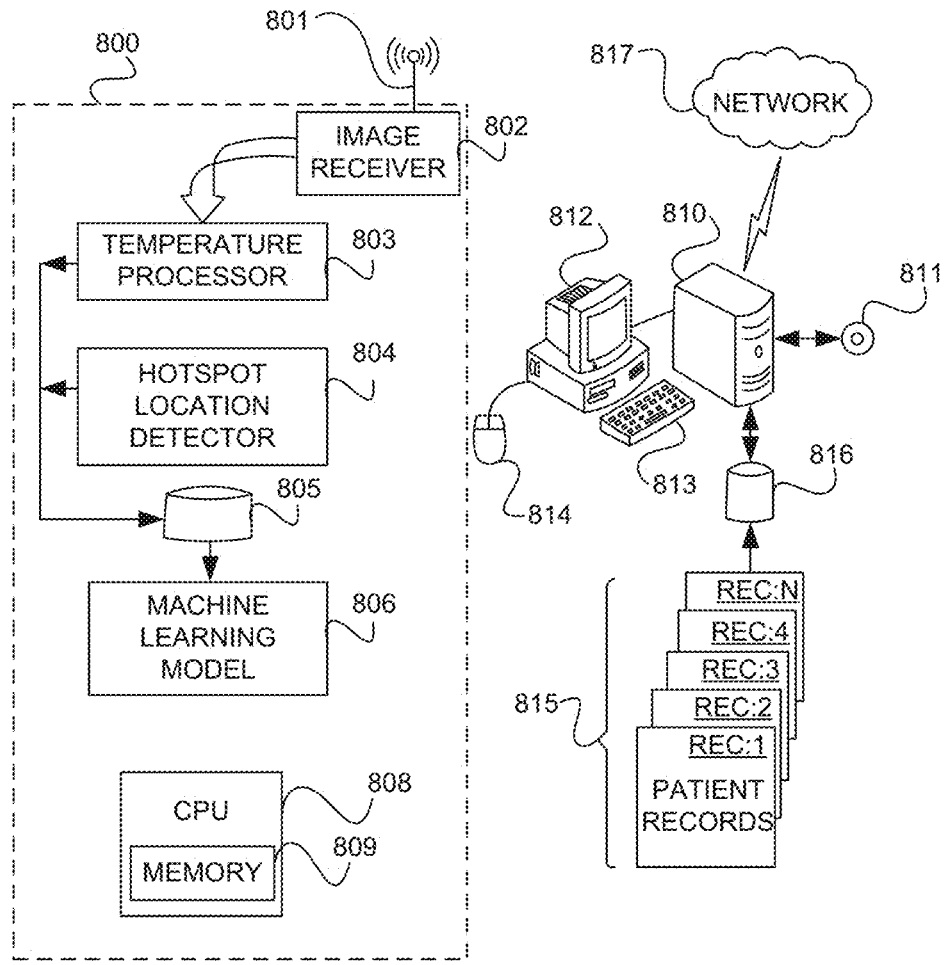
FIG. 8 illustrates a block diagram of one example system for processing a thermal image in accordance with the embodiments described with respect to the flow diagram of FIG. 7 according to some embodiments herein.

FIG. 8 illustrates a block diagram of one example system for processing a thermal image in accordance with the embodiments described with respect to the flow diagram of FIG. 7 according to some embodiments herein. Image Receiver 802 wirelessly receives the video via antenna 801 having been transmitted thereto from the video/thermal imaging device 101 of FIG. 1. Temperate Processor 803 performs a temperature-based method to detect pixels in the received image. Hotspot location detector 804 determines a location of a plurality of hotspots on the hotspot region of the thermal image from a user. Both Modules 803 and 804 store their results to storage device 805. Machine learning model 806 retrieves the results from storage device 805 and proceeds to automatically detect areolar points (x, y) from the thermal image of the breast region of the subject. The machine learning model 806 detect the location of the plurality of hotspots on the hotspot region by calculating a plurality of radial locations (ri, θi) of a plurality of hotspots on the hotspot region by estimating a radial distance (ri) and a radial angle (θi) using the areolar points (x, y) as a reference origin point. Central Processing Unit 808 retrieves machine-readable program instructions from a memory 809 and is provided to facilitate the functionality of any of the modules of the system 800. CPU 808, operating alone or in conjunction with other processors, may be configured to assist or otherwise perform the functionality of any of the modules or processing units of the system 800 as well as facilitating communication between the system 800 and the workstation 810.

System 800 is shown having been placed in communication with a workstation 810. A computer case of the workstation houses various components such as a motherboard with a processor and memory, a network card, a video card, a hard drive capable of reading/writing to machine-readable media 811 such as a floppy disk, optical disk, CD-ROM, DVD, magnetic tape, and the like, and other software and hardware needed to perform the functionality of a computer workstation. The workstation 810 further includes a display device 812, such as a CRT, LCD, or touch screen device, for displaying information, images, view angles, and the like. A user can view any of that information and make a selection from menu options displayed thereon. Keyboard 813 and mouse 814 effectuate a user input. It should be appreciated that the workstation 810 has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof. The workstation 810 is further enabled to display thermal images, the view angle of the thermal images and the like as they are derived. A user or technician may use the user interface of the workstation 810 to set parameters and adjust various aspects of the radial location calculation, quadrant estimation, radial zone estimation and clock position estimation is performed, as needed or as desired, depending on the implementation. Any of these selections or inputs may be stored retrieved to storage device 811. Default settings can be retrieved from the storage device. A user of the workstation 810 is also able to view or manipulate any of the data in the patient records, collectively at 815, stored in database 816. Any of the received images, results, determined view angle, and the like, may be stored to a storage device internal to the workstation 810. Although shown as a desktop computer, the workstation 810 can be a laptop, mainframe, or a special purpose computer such as an ASIC, circuit, or the like.

Any of the components of the workstation 810 may be placed in communication with any of the modules and processing units of system 800. Any of the modules of the system 800 can be placed in communication with storage devices 805, 816 and 806 and/or computer-readable media 811 and may store/retrieve therefrom data, variables, records, parameters, functions, and/or machine-readable/executable program instructions, as needed to perform their intended functions. Each of the modules of the system 800 may be placed in communication with one or more remote devices over network 817. It should be appreciated that some or all of the functionality performed by any of the modules or processing units of the system 800 can be performed, in whole or in part, by the workstation 810. The embodiment shown is illustrative and should not be viewed as limiting the scope of the appended claims strictly to that configuration. Various modules may designate one or more components which may, in turn, comprise software and/or hardware designed to perform the intended function.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, While the embodiments herein have been described in terms of preferred embodiments, those skilled in the art will recognize that the embodiments herein can be practiced with modification within the spirit and scope.

What is claimed is:

1. A system for automatically detecting a location of a plurality of hotspots from a thermal image of a breast region of a subject, the system comprising:
    a non-transitory storage device; and
    a processor retrieving machine-readable instructions from the non-transitory storage device which, when executed by the processor, enable the processor to:
        receive the thermal image of the breast region of the subject, which represents a temperature distribution on the breast region of the subject as pixels in the thermal image, wherein the thermal image is captured using at least one of a thermal imaging camera or a wearable device, wherein the thermal imaging camera or a wearable device comprises:
            an array of sensors that convert infrared energy into electrical signals on a per-pixel basis;
            a lens that focuses the infrared energy from the subject's breast region onto the array of sensors, wherein the array of sensors detect temperature values from the subject's breast region; and
            a specialized processor that processes the detected temperature values into at least one block of pixels to generate the thermal image;
        automatically detect areolar points (x, y) from the thermal image of the breast region of the subject;
        automatically detect a plurality of hotspot regions on the thermal image of the breast region of the subject by performing a hotspot region segmentation method, wherein the hotspot region segmentation method segments the plurality of hotspot regions from the thermal image;
        calculate a plurality of radial locations (ri, θi) of a plurality of hotspots on the hotspot region by estimating a radial distance (ri) and a radial angle (θi) using the areolar points (x, y) as a reference origin point; and
        automatically generate a text report based on the detected location of the plurality of hotspots.

2. The system of claim 1, wherein the processor is configured to train the first machine learning model by providing a plurality of thermal images and the corresponding areolar points (x, y) of different patients as training data to obtain the trained first machine learning model.

3. The system of claim 1, wherein the processor is configured to rank the plurality of hotspots on the thermal image by identifying a hotspot area, a maximum temperature, a hotspot shape, and a hotspot boundary and ranking the plurality of hotspots based on their severity or importance for generating the text report.

4. The system of claim 1, wherein the processor is configured to employ a second machine learning model that ranks the plurality of hotspots based on their severity or importance, wherein the second machine learning model is trained to identify the severe/important hotspots by providing severe/important hotspots and the corresponding ranking of different patients as training data to obtain a trained second machine learning model.

5. The system of claim 1, wherein the automatically generated text report comprises one or more modes of depicting positions of the plurality of hotspots including at least one of quadrants, clock positions, radial distance (ri), radial zone or a schematic pictorial representations calculated based on the areolar points (x, y).

6. The system of claim 5, wherein the processor is configured to identify a quadrant of each hotspot by dividing the thermal image of the breast region of the subject into four equal circular sectors using the areolar points (x, y) as a center of a reference coordinate system and using the reference coordinate system to detect the quadrant of hotspot.

7. The system of claim 5, wherein the processor is configured to identify the clock position of each hotspot by detecting an angle formed by the areolar points (x, y) and a centroid of the hotspot with the horizontal axis and converting the angle into the clock position of that hotspot.

8. The system of claim 1, wherein the processor is configured to detect the plurality of hotspot regions on the thermal image of the breast region of the subject by:
    determining a first pixel region $m_1$ within a selected region of interest with a temperature $T^1_{pixel}$, where $T_2 \leq T^1_{pixel} \leq T_1$;
    determining a second pixel region $m_2$ within the selected region of interest with a temperature $T^2_{pixel}$, where $T_3 \leq T^2_{pixel}$; and
    detecting the plurality of hotspot regions using the first pixel region $m_1$ and the second pixel region $m_2$ with AND or OR rules, wherein $T_1$, $T_2$ and $T_3$ are temperature threshold obtained from the temperature distribution.

9. The system of claim 1, wherein the processor is configured to detect the plurality of hotspot regions on the thermal image of the breast region of the subject using a third machine learning model, wherein the third machine learning model is trained by providing a plurality of thermal images and the corresponding hotspot regions associated with different patients as training data to obtain a trained third machine learning model.

10. The system of claim 5, wherein the processor is configured to generate the text report using a text conversion unit based on the radial distance, quadrant estimation, radial zone estimation and the clock position estimation, wherein the text report is updated to a database of the system along with annotated thermal images of the subject and/or schematic of the breast for providing the locations of the plurality of hotspots as a text report.

11. The system of claim 1, wherein the system is communicatively connected to a scanner and provides the detected radial locations (ri, θi) of the plurality of hotspots as the text report to scan the plurality of hotspots only on the detected radial locations (ri, θi) instead of scanning the entire breast region of the subject.

12. The system of claim 1, wherein the areolar points (x, y) are detected by at least one of (i) identifying, using an areolar detection module, a potential areolar region on the thermal image by detecting a boundary that is close to a circular or an ellipse shape in the breast region, (ii) identifying, using a first machine learning model, the areolar points (x, y) in the thermal image by providing the thermal image that is captured as an input to the first machine learning model or (iii) manually identifying the circular or the ellipse shape in the breast region.

13. A computer-implemented method for automatically detecting a location of a plurality of hotspots from a thermal image of a breast region of a subject, the method comprising:
  receiving the thermal image of a body of a subject, which represents a temperature distribution on the body of the subject as pixels in the thermal image, wherein the thermal image is captured using at least one of a thermal imaging camera or a wearable device, wherein the thermal imaging camera or a wearable device comprises:
    an array of sensors that convert infrared energy into electrical signals on a per-pixel basis;
    a lens that focuses the infrared energy from the subject's breast region onto the array of sensors, wherein the array of sensors detect temperature values from the subject's breast region; and
    a specialized processor that processes the detected temperature values into at least one block of pixels to generate the thermal image;
  automatically detect areolar points (x, y) from the thermal image of the breast region of the subject;
  automatically detecting areolar points (x, y) from the thermal image of the breast region of the subject;
  automatically detecting a plurality of hotspot regions on the thermal image of the breast region of the subject by performing a hotspot region segmentation method, wherein the hotspot region segmentation method segments the plurality of hotspot regions from the thermal image;
  calculating a plurality of radial locations (ri, θi) of a plurality of hotspots on the hotspot region by estimating a radial distance (ri) and a radial angle (θi) using the areolar points (x, y) as a reference origin point; and
  automatically generating a text report based on the detected location of the plurality of hotspots.

14. The computer-implemented method of claim 13, wherein the areolar points (x, y) are detected by at least one of (i) identifying, using an areolar detection module, a potential areolar region on the thermal image by detecting a boundary that is close to a circular or an ellipse shape in the breast region, (ii) identifying, using a first machine learning model, the areolar points (x, y) in the thermal image by providing the thermal image that is captured as an input to the first machine learning model or (iii) manually identifying the circular or the ellipse shape in the breast region.

15. The computer-implemented method of claim 13, wherein the first machine learning model is trained by providing a plurality of thermal images and the corresponding areolar points (x, y) of different patients as training data to obtain the trained first machine learning model.

16. The computer-implemented method of claim 13, wherein the method comprises ranking the plurality of hotspots on the thermal image by identifying a hotspot area, a maximum temperature, a hotspot shape, and a hotspot boundary and ranking the plurality of hotspots based on their severity or importance for generating the text report.

17. The computer-implemented method of claim 13, wherein the method comprises employing a second machine learning model that ranks the plurality of hotspots based on their severity or importance, wherein the second machine learning model is trained to identify the severe/important hotspots by providing severe/important hotspots and the corresponding ranking of different patients as training data to obtain a trained second machine learning model.

18. The computer-implemented method of claim 13, wherein the method comprises identifying a quadrant of each hotspot by dividing the thermal image of the breast region of the subject into four equal circular sectors using the areolar points (x, y) as a centre of a reference coordinate system and using the reference coordinate system to detect the quadrant of the hotspot.

19. The computer-implemented method of claim 13, wherein the hotspot regions on the thermal image of the breast region of the subject are detected by:
  determining a first pixel region $m_1$ within a selected region of interest with a temperature $T^1_{pixel}$, where $T_2 \leq T^1_{pixel} \leq T_1$;
  determining a second pixel region $m_2$ within the selected region of interest with a temperature $T^2_{pixel}$, where $T_3 \leq T^2_{pixel}$; and
  detecting the plurality of hotspot regions using the first pixel region $m_1$ and the second pixel region $m_2$ with AND or OR rules, wherein $T_1$, $T_2$ and $T_3$ are temperature threshold obtained from the temperature distribution.

20. The computer-implemented method of claim 13, wherein the method comprises providing the detected radial locations (ri, θi) of the plurality of hotspots as the text report to a device to scan the plurality of hotspots only on the detected radial locations (ri, θi) instead of scanning the entire breast region of the subject, wherein the plurality of hotspot regions on the thermal image of the breast region of the subject are detected using a third machine learning model, wherein the third machine learning model is trained by providing a plurality of thermal images and the corresponding hotspot regions associated with different patients as training data to obtain a trained third machine learning model.

* * * * *